(12) United States Patent
Yamamoto et al.

(10) Patent No.: US 9,399,143 B2
(45) Date of Patent: Jul. 26, 2016

(54) ANTENNA FOR IMPLANTABLE MEDICAL DEVICES FORMED ON EXTENSION OF RF CIRCUIT SUBSTRATE AND METHOD FOR FORMING THE SAME

(75) Inventors: Joyce K. Yamamoto, Maple Grove, MN (US); Quentin Scott Denzene, Andover, MN (US); Michael William Barror, Gilbert, AZ (US)

(73) Assignee: Medtronic, Inc., Minneapolis, MN (US)

( * ) Notice: Subject to any disclaimer, the term of this patent is extended or adjusted under 35 U.S.C. 154(b) by 2071 days.

(21) Appl. No.: 12/340,509

(22) Filed: Dec. 19, 2008

(65) Prior Publication Data

US 2010/0114245 A1 May 6, 2010

Related U.S. Application Data

(60) Provisional application No. 61/110,534, filed on Oct. 31, 2008.

(51) Int. Cl.
*A61N 1/00* (2006.01)
*A61N 1/372* (2006.01)
(Continued)

(52) U.S. Cl.
CPC .......... *A61N 1/37229* (2013.01); *H01Q 1/2283* (2013.01); *H01Q 21/28* (2013.01); *Y10T 29/49016* (2015.01)

(58) Field of Classification Search
CPC .. A61N 1/37229; H01Q 1/2283; H01Q 21/28
USPC ......................................................... 607/60
See application file for complete search history.

(56) References Cited

U.S. PATENT DOCUMENTS

| 5,023,624 A | 6/1991 | Heckaman et al. |
| 5,198,824 A | 3/1993 | Poradish |
| 5,219,377 A * | 6/1993 | Poradish ........................ 29/830 |

(Continued)

FOREIGN PATENT DOCUMENTS

| CN | 1876200 | 12/2006 |
| CN | 101267777 | 9/2008 |

(Continued)

OTHER PUBLICATIONS (PCT/US09/061834) PCT Notification of Transmittal of the International Search Report and the Written Opinion of the International Searching Authority, 11 pages.

(Continued)

*Primary Examiner* — Christopher D Koharski
*Assistant Examiner* — Michael D Abreu (57) ABSTRACT

An antenna for an implantable medical device (IMD) is provided that is formed on the same substrate as the telemetry circuitry for the IMD. The telemetry circuitry is formed on a portion of the substrate within the interior of a housing for the IMD, while at least one antenna is formed on an exterior portion of the substrate on the exterior of the housing to allow for far field telemetry. At least one electrical interconnect is formed on the substrate for connecting the antenna to the telemetry circuitry, where the electrical interconnect may comprise a controlled impedance line to minimize loss. A conformally-shaped hermetic cover, such as a ceramic material, may be formed in a desired shape around the exterior portion of the substrate and antenna and cofired together to form a monolithic structure encasing the antenna and exterior portion of the substrate.

15 Claims, 8 Drawing Sheets

(51) Int. Cl.
*H01Q 1/22* (2006.01)
*H01Q 21/28* (2006.01)

(56) References Cited

U.S. PATENT DOCUMENTS

| | | | |
|---|---|---|---|
| 5,387,888 A | 2/1995 | Eda et al. | |
| 5,620,476 A | 4/1997 | Truex et al. | |
| 5,683,435 A | 11/1997 | Truex et al. | |
| 5,861,019 A | 1/1999 | Sun et al. | |
| 6,107,227 A | 8/2000 | Jacquin et al. | |
| 6,320,547 B1 | 11/2001 | Fathy et al. | |
| 6,391,082 B1 | 5/2002 | Holl | |
| 6,414,835 B1 | 7/2002 | Wolf et al. | |
| 6,556,169 B1 | 4/2003 | Fukuura et al. | |
| 6,580,402 B2 | 6/2003 | Navarro et al. | |
| 7,012,327 B2 | 3/2006 | Huff et al. | |
| 7,122,891 B2 | 10/2006 | Dishongh | |
| 7,164,572 B1 | 1/2007 | Burdon et al. | |
| 7,289,063 B2 | 10/2007 | Zaghloul | |
| 7,317,946 B2 | 1/2008 | Twetan et al. | |
| 7,392,015 B1 * | 6/2008 | Farlow et al. | 455/67.11 |
| 2005/0113886 A1 | 5/2005 | Fischell et al. | |
| 2006/0212096 A1 | 9/2006 | Stevenson | |
| 2006/0214855 A1 | 9/2006 | Harada | |
| 2006/0247712 A1 * | 11/2006 | Fuller et al. | 607/32 |
| 2007/0200706 A1 | 8/2007 | Lee | |
| 2007/0236861 A1 | 10/2007 | Burdon et al. | |
| 2008/0021522 A1 * | 1/2008 | Verhoef et al. | 607/60 |
| 2008/0103558 A1 | 5/2008 | Wenzel et al. | |

FOREIGN PATENT DOCUMENTS

| | | |
|---|---|---|
| EP | 1362614 A1 | 11/2003 |
| GB | 2414408 A | 11/2005 |
| WO | WO/01/02468 | 1/2001 |
| WO | 2007065140 A2 | 6/2007 |
| WO | 2008112578 A1 | 9/2008 |

OTHER PUBLICATIONS

Caiazzo, et al., A Metamaterial Surface for Compact Cavity Resonators, IEEE AP Letters, 2004, pp. 261-264, vol. 3.

Wu, et al., A study Using Metamaterials as Antenna Substrate to Enhance Gain, Pier 51, 2005, pp. 295-328.

Mosallaei, et al, Antenna Miniaturization and Bandwidth Enhancement Using a Reactive Impedance Substrate, IEEE APS, Sep. 2004, pp. 2403-2414, vol. 52 No. 9.

Broas, et al., A High Impedance Ground Plane Applied to a Cellphone Handset Geometry, IEEE MTT, Jul. 2001, pp. 1262-1265, vol. 49 No. 7.

Lal C. Godara, Application of Antenna Arrays to Mobile Communications, Part I: Performance Improvement, Feasibility, and System Considerations, Proceedings of the IEEE, Jul. 1997, pp. 1031-1060, vol. 85, No. 7.

Lal C. Godara, Application of Antenna Arrays to Mobile Communications, Part II: Beam-forming and Direction-of-Arrival Considerations, Proceedings of the IEEE, Aug. 1997, pp. 1195-1245, vol. 85, No. 8.

The State Intellectual Property Office of the People's Republic of China; "Notice on the First Office Action"; Application No. 200980143802.5; Jun. 3, 2013, 14 pages.

* cited by examiner

ANTENNA FOR IMPLANTABLE MEDICAL DEVICES FORMED ON EXTENSION OF RF CIRCUIT SUBSTRATE AND METHOD FOR FORMING THE SAME

RELATED APPLICATION

This application claims the benefit of and priority to U.S. Provisional Application Ser. No. 61/110,534, filed Oct. 31, 2008, entitled, "Antenna for Implantable Medical Devices Formed on Extension of RF Circuit Substrate and Method for Forming the Same," the contents of which are incorporated by reference herein in its entirety.

TECHNICAL FIELD

The present invention relates generally to implantable medical devices (IMDs) and, more particularly, the present invention relates to telemetry antennas suitable for deployment in IMDs.

BACKGROUND

Various types of devices have been developed for implantation into the human body to provide various types of health-related therapies, diagnostics and/or monitoring. Examples of such devices, generally known as implantable medical devices (IMDs), include cardiac pacemakers, cardioverter/defibrillators, cardiomyostimulators, cardiac event monitors, various physiological stimulators including nerve, muscle, and deep brain stimulators, various types of physiological monitors and sensors, and drug delivery systems, just to name a few. IMDs typically include functional components contained within a hermetically sealed enclosure or housing, which is sometimes referred to as a "can." In some IMDs, a connector header or connector block is attached to the housing, and the connector block facilitates interconnection with one or more elongated electrical medical leads. The header block is typically molded from a relatively hard, dielectric, non-conductive polymer. The header block includes a mounting surface that conforms to, and is mechanically affixed against, a mating sidewall surface of the housing.

It has become common to provide a communication link between the electronic circuitry hermetically sealed within the can of the IMD and an external programmer, monitor, or other external medical device ("EMD") in order to provide for downlink telemetry transmission of commands from the EMD to the IMD and to allow for uplink telemetry transmission of stored information and/or sensed physiological parameters from the IMD to the EMD. Conventionally, the communication link between the IMD and the EMD is realized by encoded radio frequency ("RF") transmissions between an IMD telemetry antenna and transceiver and an EMD telemetry antenna and transceiver. Generally, the IMD antenna is disposed within the hermetically sealed housing. However, the typically conductive housing can limit the radiation efficiency of the IMD RF telemetry antenna, thereby traditionally limiting the data transfer distance between the EMD and the IMD RF telemetry antennas to a few inches. This type of system may be referred to as a "near field" telemetry system. In order to provide for "far field" telemetry, or telemetry over distances of a few to many meters from an IMD or even greater distances, attempts have been made to provide antennas outside of the hermetically sealed housing and within the header block. Many of such attempts of positioning an RF telemetry antenna outside of the hermetically sealed housing and in the header block have utilized wire antennas or planar, serpentine antennas, such as the antennas described in U.S. Pat. No. 7,317,946, which is hereby incorporated by reference in its entirety. However, the positioning of the antenna in the header block outside of the can has conventionally required the antenna to be connected to electronic circuitry in the IMD through complicated electrical feedthroughs that extend through the hermetically sealed can.

SUMMARY

In one or more embodiments, an antenna for an implantable medical device (IMD) is provided that is formed on the same substrate as the telemetry circuitry for the IMD. The telemetry circuitry for the IMD is formed on or otherwise connected to an interior portion of the substrate that is situated within an interior portion of a housing for the IMD. The substrate further includes an exterior portion that extends outside of the housing. The antenna is formed on the exterior portion of the substrate at a location exterior to the housing. At least one electrical interconnect is formed on the substrate extending from the exterior portion of the housing to the interior portion for connecting the antenna on the exterior of the housing to the telemetry circuitry within the interior of the housing. In some embodiments, the substrate may comprise a printed wiring board (PWB) or ceramic substrate material and the electrical interconnect may comprise printed wiring formed on the substrate. In some embodiments, the electrical interconnect may comprise a controlled impedance line to minimize loss between the antenna and the telemetry circuitry.

In one or more embodiments, a plurality of antennas may be formed on the exterior portion of the substrate, such that different antennas or combinations of antennas can be selected and/or switched for use in order to provide a tunable antenna to suit the needs of the particular IMD and/or the particular implant location. In some embodiments, different antennas may be formed on different locations of the exterior portion of the substrate (e.g., opposite sides of the substrate) to allow for communication in multiple possible directions from the IMD, such that different antennas can be selected and/or switched for use based on the ultimate location or position in which the IMD is implanted within a patient. In some embodiments, the antenna may be positioned at an end portion of the exterior portion of the substrate so that the antenna can transmit and receive telemetry signals in multiple directions from the IMD.

In one or more embodiments, a hermetic covering may be positioned around the exterior portion of the substrate to cover the antenna and provide a hermetic seal around the antenna and the exterior portion of the substrate. In some embodiments, the hermetic covering may comprise a material conformally shaped based on a desired implantation location for the IMD. In one or more embodiments, the hermetic covering comprises a cofired ceramic material, such that the cofired ceramic material can be formed in a desired shape to provide additional support for the exterior portion of the substrate or to provide desired transmission characteristics for the antenna. In some embodiments, the antenna may be embedded within the ceramic material and cofired together to form a monolithic structure encasing the antenna and exterior portion of the substrate. In some embodiments, the cofired ceramic material comprises a high temperature co-fire ceramic (HTCC) material having a melting point between about 1100° C. and 1700° C., wherein the ceramic material and the antenna are cofired together at such temperatures to form the monolithic structure encasing the antenna and exterior portion of the substrate.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The following detailed description is merely illustrative and is not intended to limit the invention or the application and uses of the invention. Furthermore, there is no intention to be bound by any expressed or implied theory presented in the preceding technical field, background, brief summary or the following detailed description.

The following description may refer to components or features being "connected" or "coupled" together. As used herein, unless expressly stated otherwise, "connected" means that one component/feature is directly or indirectly connected to another component/feature, and not necessarily mechanically. Likewise, unless expressly stated otherwise, "coupled" means that one component/feature is directly or indirectly coupled to another component/feature, and not necessarily mechanically. Thus, although the figures may depict example arrangements of elements, additional intervening elements, devices, features, or components may be present in an actual embodiment (assuming that the functionality of the IMDs are not adversely affected).

In one or more embodiments, an IMD having an improved antenna structure is provided. For the sake of brevity, conventional techniques and aspects related to RF antenna design, IMD telemetry, RF data transmission, signaling, IMD operation, connectors for IMD leads, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

An IMD antenna generally has two functions: to convert the electromagnetic power of a downlink telemetry transmission of an EMD telemetry antenna propagated through the atmosphere (and then through body tissues) into a signal (e.g., a UHF signal or the like) that can be processed by the IMD transceiver into commands and data that are intelligible to the IMD electronic operating system; and to convert the uplink telemetry signals (e.g., a UHF signal or the like) of the IMD transceiver electronics into electromagnetic power propagated through the body tissue and the atmosphere so that the EMD telemetry antenna or antennas can receive the signals.

Figure 1:
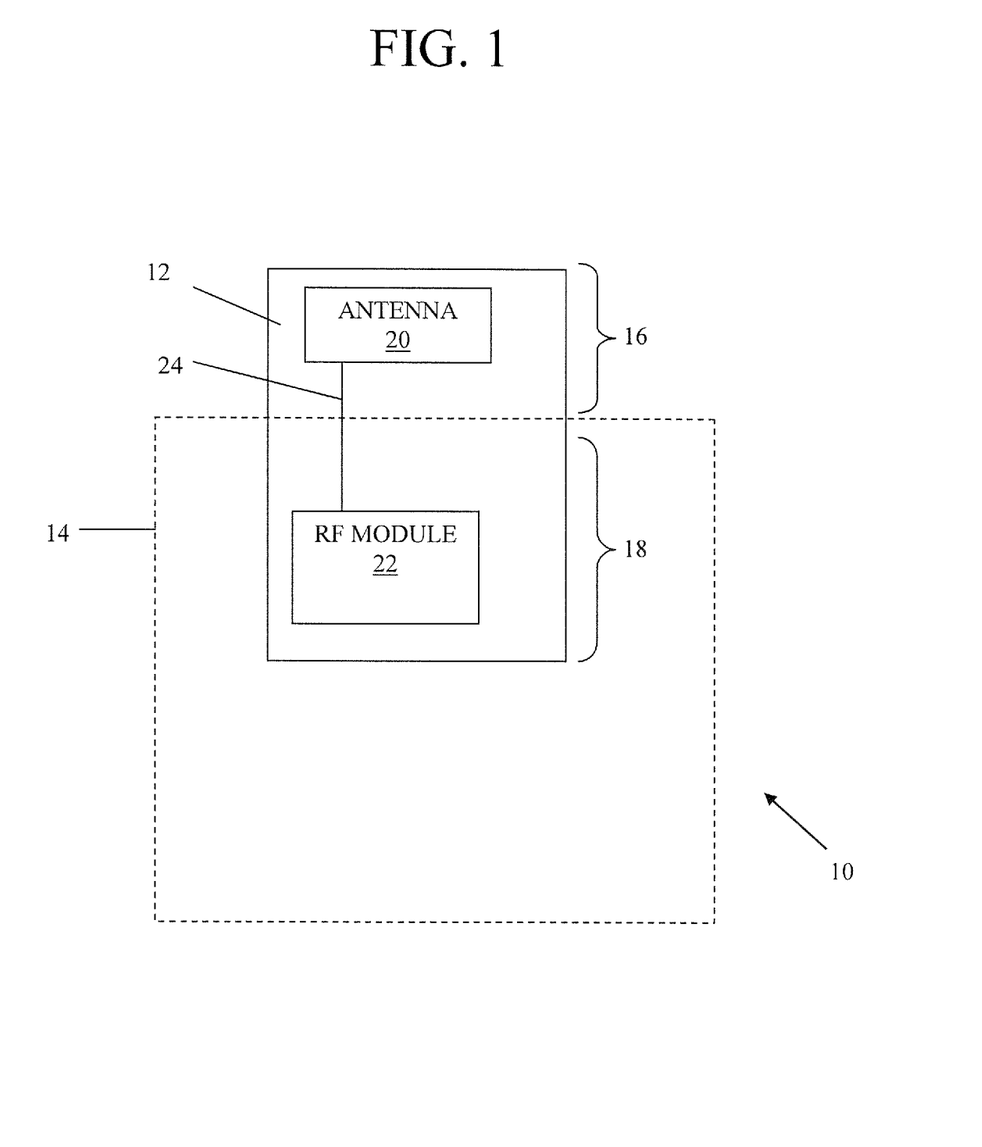
FIG. 1 is a top view of a schematic block diagram illustration of an exemplary implantable medical device in accordance with one or more embodiments of the present disclosure.

FIG. 1 is a simplified schematic representation of an IMD 10 and several functional elements associated therewith. IMD 10 includes hermetically sealed housing 14 and a substrate 12 on which circuitry and other functional components for IMD 10 are formed. In one or more embodiments, substrate 12 includes an interior portion 18 that is positioned within an interior portion of housing 14 and an exterior portion 16 that extends outside of housing 14. An antenna 20 for IMD 10 is formed on the exterior portion 16 of substrate 12 at a location exterior to housing 14 to allow for far field telemetry operations. In one or more embodiments, antenna 20 is formed from a biocompatible conductive material, such as but not limited to at least one of the following materials: Platinum, Iridium, Platinum-Iridium alloys, Alumina, Silver, Gold, Palladium, Silver-Palladium or mixtures thereof, or Niobium, Molybdenum and/or Moly-manganese or other suitable materials.

A telemetry RF module 22 or other telemetry circuitry is positioned within housing 14 and is formed on the interior portion 18 of substrate 12, such that antenna 20 and RF module 22 are formed on the same substrate 12. At least one electrical interconnect 24 is formed on substrate 12 extending from exterior portion 16 of substrate 12 to interior portion 18 of substrate 12 for connecting antenna 20 on the exterior of housing 14 to RF module 22 within the interior of housing 14. In this manner, the at least one electrical interconnect 24 extends from a portion outside of housing 14 to a portion inside of housing 14. In one or more embodiments, substrate 12 comprises a printed wiring board (PWB) or other type of circuit board, wherein electrical interconnect 24 comprises printed wiring formed on the PWB. In some embodiments, electrical interconnect 24 may comprise a controlled impedance line to minimize loss in signals that are communicated between antenna 20 and RF module 24.

Further, in practice, IMD 10 will also include a number of conventional components and features necessary to support the functionality of IMD 10 as known in the art, such as a therapy module, a controller, a memory, a power supply, etc. The operation of these and other conventional elements will not be described herein.

RF module 22 may include any number of components, including, without limitation: electrical devices, ICs, amplifiers, signal generators, a receiver and a transmitter (or a transceiver), modulators, microprocessors, controllers, memories, power supplies, and the like. RF module 22 may further include a matching circuit or a matching circuit may be positioned between RF module 22 and antenna 20. A matching circuit may include any number of components, including, without limitation: electrical components such as capacitors, resistors, or inductors; filters; baluns; tuning elements; varactors; limiter diodes; or the like, that are all suitably configured to provide impedance matching between antenna 20 and RF module 22, thus improving the efficiency of antenna 20. Briefly, RF module 22 supports RF telemetry communication for IMD 10, including, without limitation: generating RF transmit energy; providing RF transmit signals to antenna 20; processing RF telemetry signals received by antenna 20, and the like. For some applications, RF module 22 may be designed to leverage the conductive material used for housing 14 as an RF ground plane, and RF module 22 may be designed in accordance with the intended application of IMD 10, the electrical characteristics of the environment surrounding the implant location, the desired operating frequency range, the desired RF antenna range, and other practical considerations.

Antenna 20 is coupled to RF module 22 by electrical interconnect 24 to facilitate RF telemetry between IMD 10 and an external device. Generally, antenna 20 is suitably configured for RF operation (e.g., UHF or VHF operation, 401 to 406 MHz for the MICS/MEDS bands, 900 MHz/2.4 GHz and other ISM bands, etc.). Antenna 20 may have characteristics resembling a monopole antenna, characteristics resembling a dipole antenna, characteristics resembling a coplanar waveguide antenna, characteristics resembling a stripline antenna, characteristics resembling a microstrip antenna, and/or characteristics resembling a transmission line antenna. Antenna 20 may also have any number of radiating elements, which may be driven by any number of distinct RF signal sources. In this regard, antenna 20 may have a plurality of radiating elements configured to provide spatial or polarization diversity Referring now to FIG. 2, a perspective, partial cutaway view of an exemplary IMD 10 is illustrated in accordance with one or more embodiments in which antenna 20 and RF module 22 are positioned on respective exterior and interior portions 16 and 18 of the same substrate 12. In one or more embodiments, the use of a common substrate 12 for the circuitry components of both antenna 20 and RF module 22 allow for far field communications using the antenna 20 without the requirement of a separate antenna assembly that conventionally has been required to be attached to the exterior of an IMD and then connected to interior electronics through feedthrough connections. Rather, a direct connection between antenna 20 and RF module 22 can be achieved through simple printed wiring traces (i.e., electrical interconnect 24) along a surface of substrate 12 or buried within substrate 12. In some embodiments, these printed wiring traces (i.e., electrical interconnect 24) can be controlled impedance lines to minimize loss in the signals communicated between antenna 20 and RF module 22.

Figure 2:
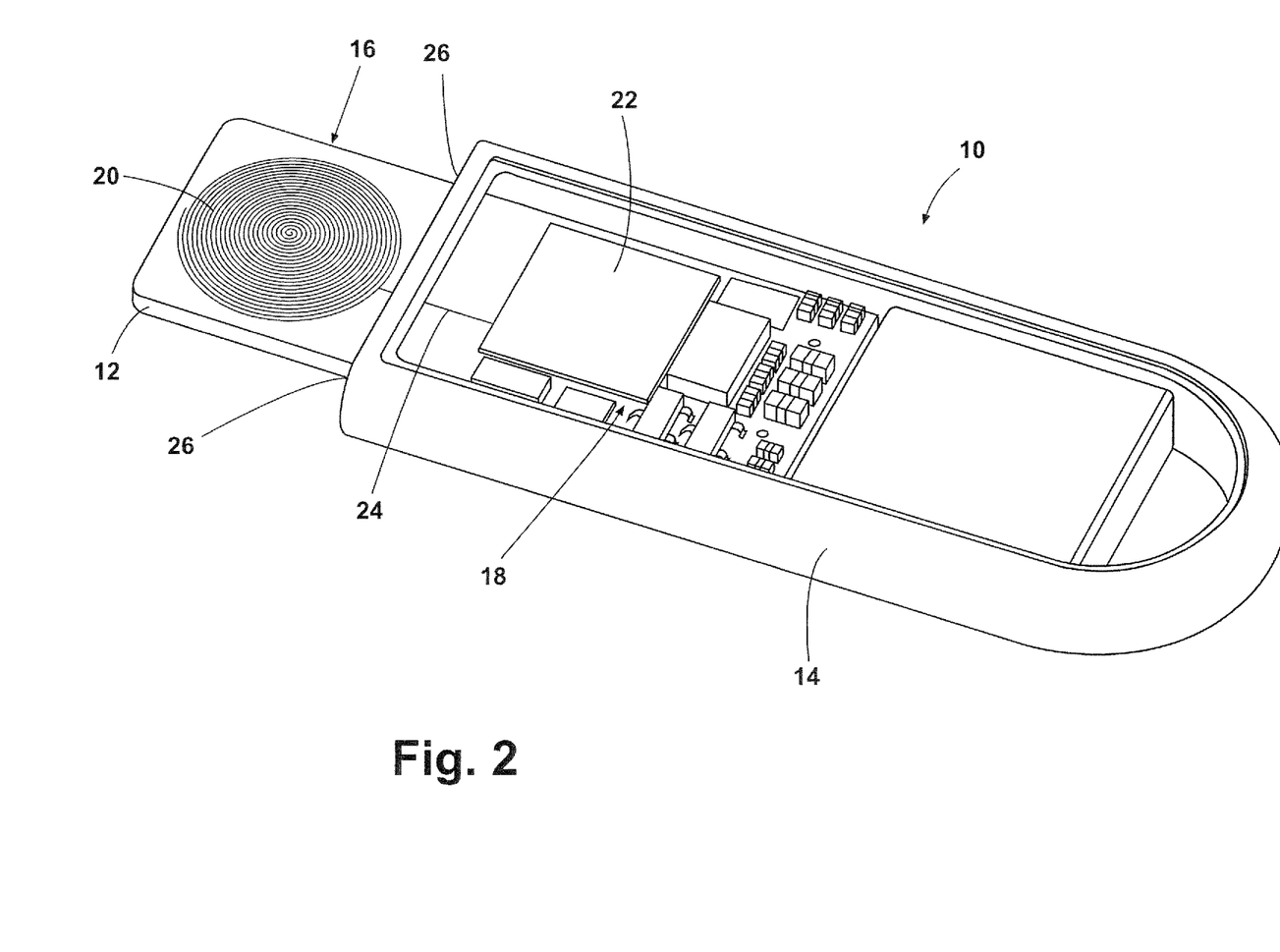
FIG. 2 is a perspective, partial cutaway view of an exemplary implantable medical device in accordance with one or more embodiments of the present disclosure.

In one or more embodiments, antenna 20 can thus be positioned at a location on exterior portion 16 of substrate 12 that is spaced apart a desired distance from housing 14 to achieve a desirable radiation efficiency. Housing 14 is typically formed from a conductive material that can limit the radiation efficiency of the IMD RF telemetry antenna 20, thereby serving to limit the data transfer distance for the antenna 20 for RF telemetry operations. Improved far field telemetry operations can be achieved by situating antenna 20 a desired distance away from the surface of housing 14, while still providing a direct, controlled impedance electrical interconnect 24 between antenna 20 and RF module 22.

Figure 4:
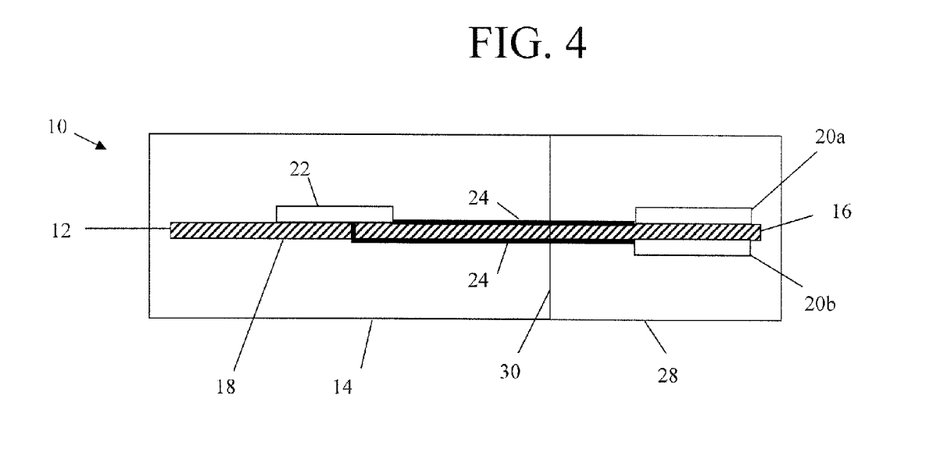
FIG. 4 is a side, partial cutaway view of another exemplary implantable medical device in accordance with one or more embodiments of the present disclosure.
Figure 5:
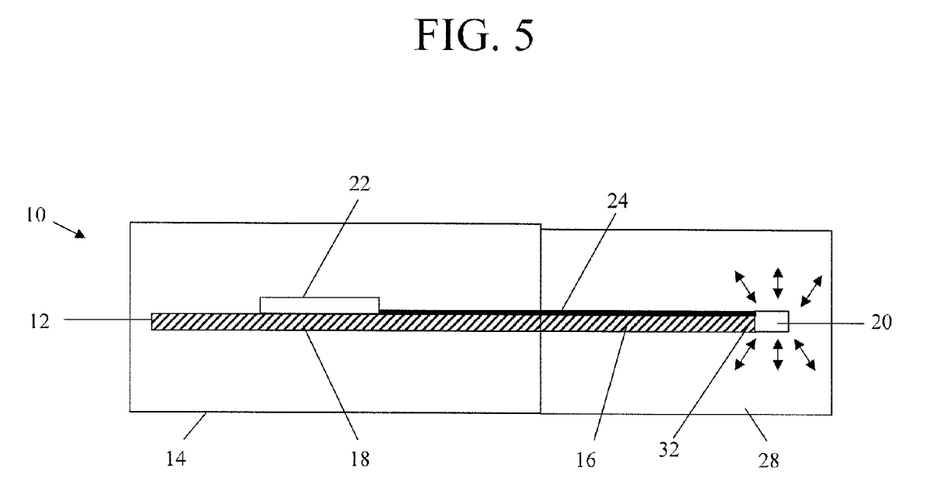
FIG. 5 is a side, partial cutaway view of another exemplary implantable medical device in accordance with one or more embodiments of the present disclosure.

In one or more embodiments, housing 14 is hermetically sealed and is generally circular, elliptical, prismatic, or rectilinear, with substantially planar major sides joined by perimeter sidewalls. Housing 14 is typically formed from pieces of a thin-walled biocompatible metal such as titanium or like, where two half sections of housing 14 may be laser seam welded together using conventional techniques to form a seam extending around the perimeter sidewalls. This seam weld can further be extended at locations 26 adjacent to where substrate 12 extends from the interior of housing to its exterior, such that substrate 12 can itself be seam welded or otherwise hermetically sealed to housing 14 at their junction where they intersect and where substrate 12 extends through housing 14. Housing 14 can further alternatively be formed as a seamless deep drawn can. In this manner, a hermetic seal can be established between substrate 12 and housing 14. In one or more embodiments, exterior portion 16 of substrate 12 and antenna 20 may further be hermetically sealed within a header 28 (as shown in FIGS. 4 and 5) or embedded within a surrounding ceramic or other suitable material (as shown in FIGS. 6A, 6B, 7A and 7B), in order to hermetically seal and isolate such exterior portion 16 of substrate 12 and antenna 20 from the surrounding environment within a patient's body of the implant location of IMD 10.

Figure 3:
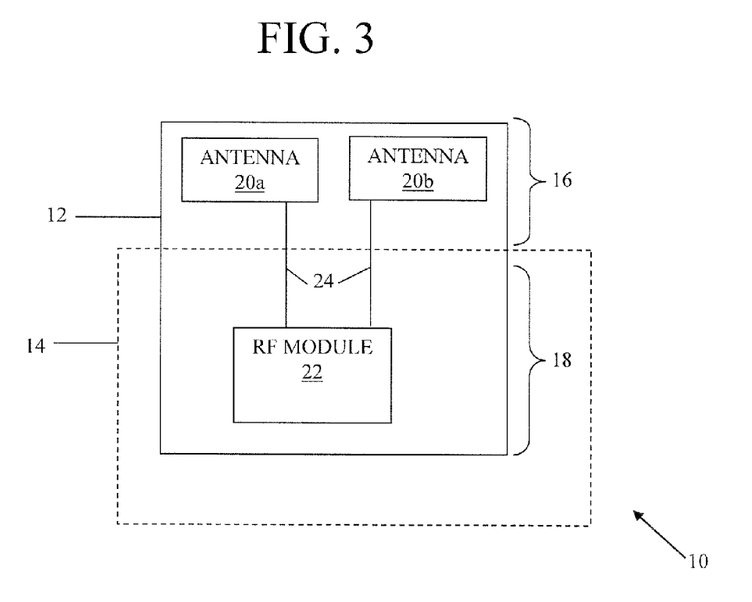
FIG. 3 is a top view of a schematic block diagram illustration of another exemplary implantable medical device in accordance with one or more embodiments of the present disclosure.

Referring now to FIG. 3, a schematic block diagram illustration of another exemplary IMD 10 is provided in accordance with one or more embodiments of the present disclosure in which multiple antennas 20 (e.g., 20a, 20b, etc.) may be positioned on exterior portion 16 of substrate 12 and connected to RF module 22 through electrical interconnects 24. By utilizing multiple antennas 20, different respective antennas 20 can be selected for use based on the desired operating characteristics for antenna 20. In this manner, different antennas 20 can be selected to provide a specific desired radiation polarization, such that the selected antenna 20 can be controlled to provide x-polarized, y-polarized and/or even circular polarizations with the simple toggling of switches (not shown) to reconfigure the connection of RF module 22 to the appropriate antenna 20 to provide the desired performance. In one or more embodiments, MEMS switches or other switches may be utilized and located on substrate 24 for performing such antenna switching. Further, different antennas 20 can be selected to change operating frequencies by selectively switching the particular antennas 20 that have different characteristics or in order to increase or decrease the resultant antenna length. Still further, different antennas 20 can be selected for use based on the surrounding environment and can be switched to suit the needs of the particular IMD 10 and/or the particular implant location. By way of example and not limitation, multiple different possible types of antenna arrangements for any of the antennas 20 that may be formed on substrate 12 are illustrated in FIGS. 8A-8G in accordance with one or more embodiments.

In one or more embodiments, multiple antennas 20 may be formed on different respective locations of exterior portion 16 of substrate 12 in order to allow for communication in different desired directions or a multitude of possible directions. For example, antennas 20a and 20b can be situated on opposite surfaces of exterior portion 16 of substrate 12, as illustrated in FIG. 4, in order to allow for one of the respective antennas 20a and 20b to be selected for optimal RF telemetry based on the manner location and direction in which the particular IMD 10 is implanted within a patient. This provides physicians with greater flexibility in implanting IMD 10 within a patient. In some embodiments, antenna 20 may be positioned at an end 32 of exterior portion 16 of substrate 12, as illustrated in FIG. 5, so that antenna 20 can transmit and receive telemetry signals in multiple or substantially all directions from IMD 10.

Figure 6A:
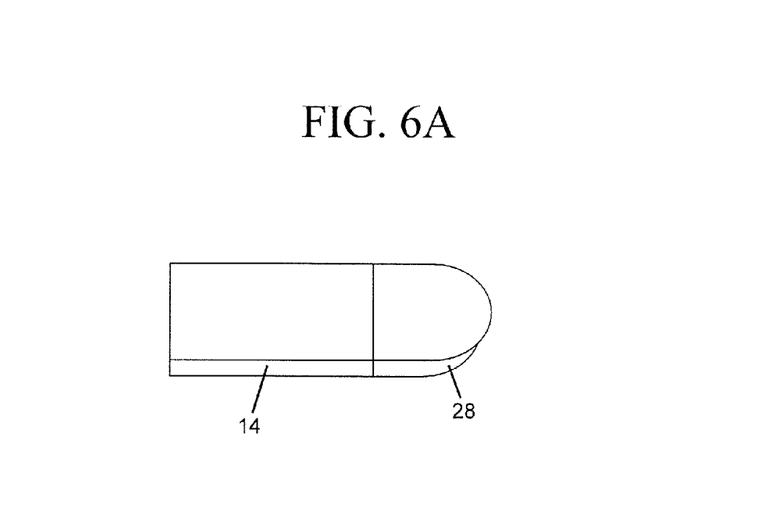
FIG. 6A is a perspective view of an exemplary implantable medical device having a cofired, conformally-shaped antenna portion in accordance with one or more embodiments of the present disclosure.

In one or more embodiments, a hermetic covering 28 may be positioned around exterior portion 16 of substrate 12 to cover antenna 20 or other components external to housing 14 and to provide a hermetic seal around antenna 20 and exterior portion 16 of the substrate 12, as illustrated in the perspective view of FIG. 6A. In some embodiments, hermetic covering 28 may be formed from a suitable dielectric material, such as a biocompatible synthetic polymer. In some embodiments, the dielectric material of hermetic covering 28 may be selected to enable the passage of RF energy that is either radiated or received by telemetry antenna 20 encapsulated within hermetic covering 28. The specific material for hermetic covering 28 may be chosen in response to the intended application of IMD 10, the electrical characteristics of the environment surrounding the implant location, the desired operating frequency range, the desired RF antenna range, and other practical considerations.

Figure 6B:
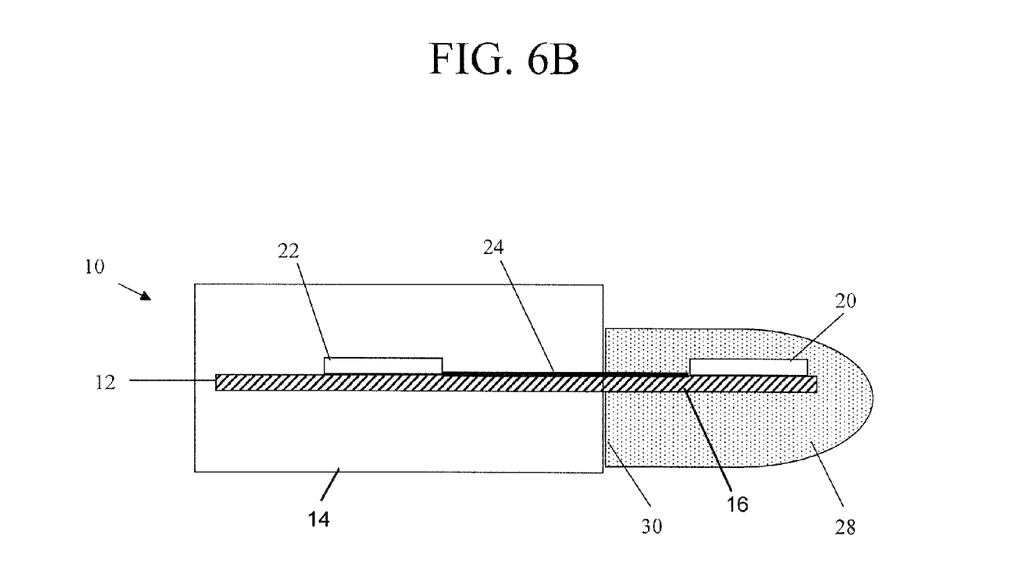
FIG. 6B is a side, partial cutaway view of the exemplary implantable medical device of FIG. 6A.

In one or more embodiments, hermetic covering 28 may comprise a cofired ceramic material that may be formed to completely encase exterior portion 16 of substrate 12 and antenna 20, as illustrated by the partial cross-sectional side view of FIG. 6B. The junction 30 between hermetic covering 28 and housing 14 may be then be sealed by brazing, glassing, diffusion bonding or other suitable bonding techniques that will provide a hermetic seal, as known to those skilled in the art. Generally, brazing involves melting and flowing a brazing material (e.g., a metal such as gold) around the portions of the desired surfaces to be brazed (e.g., the junction 30 between hermetic covering 28 and housing 14).

In one or more embodiments, the use of a cofired ceramic material allows hermetic covering 28 to be specially designed and shaped for desired characteristics of IMD 10. In one aspect, the use of a cofired ceramic material allows hermetic covering 28 to be conformally shaped (e.g., curved) to conform to a desired or required shape for a particular implant location. In another aspect, the use of a cofired ceramic material allows hermetic covering 28 to specially shaped to provide additional or desired support and stability for exterior portion 16 of substrate 12. In another aspect, the use of a cofired ceramic material allows hermetic covering 28 to specially shaped to provide a desired passage of RF energy that is either radiated or received by telemetry antenna 20 encapsulated within hermetic covering 28. In some embodiments, antenna 20 may be embedded within the ceramic material used to form hermetic covering 28 and cofired together to form a monolithic structure on the exterior of housing 14 encasing antenna 20 and exterior portion 16 of substrate 12.

In one or more embodiments, the cofired ceramic material for hermetic covering 28 comprises a high temperature co-fire ceramic (HTCC) material having a melting point between about 1100° C. and 1700° C., wherein the ceramic material and antenna 20 are cofired together at such temperatures to form the monolithic structure 28 encasing antenna 20 and exterior portion 16 of substrate 12. In one or more embodiments, the cofired ceramic material for hermetic covering 28 comprises a low temperature co-fired ceramic (LTCC) material having melting point between about 850° C. and 1150° C. Methods for co-firing layers of ceramic materials together to form monolithic structures for use in IMDs are described, for example, in U.S. Pat. No. 6,414,835 and U.S. Pat. No. 7,164, 572, the contents of both of which are hereby incorporated by reference in their entireties.

According to one or more embodiments, the use of a cofiring technique to form a monolithic structure for hermetic covering 28 that includes the embedded antenna 20 allows for the manufacture of low-cost, miniaturized, hermetically sealed antenna structures suitable for implantation within tissue and/or in direct or indirect contact with diverse body fluids. Further, the ceramic materials used to form hermetic covering 28 can be loaded with powders of a desired dielectric constant so as to produce a structure having a desired effective dielectric value that is situated between antenna 20 and the surrounding environment.

Figure 7A:
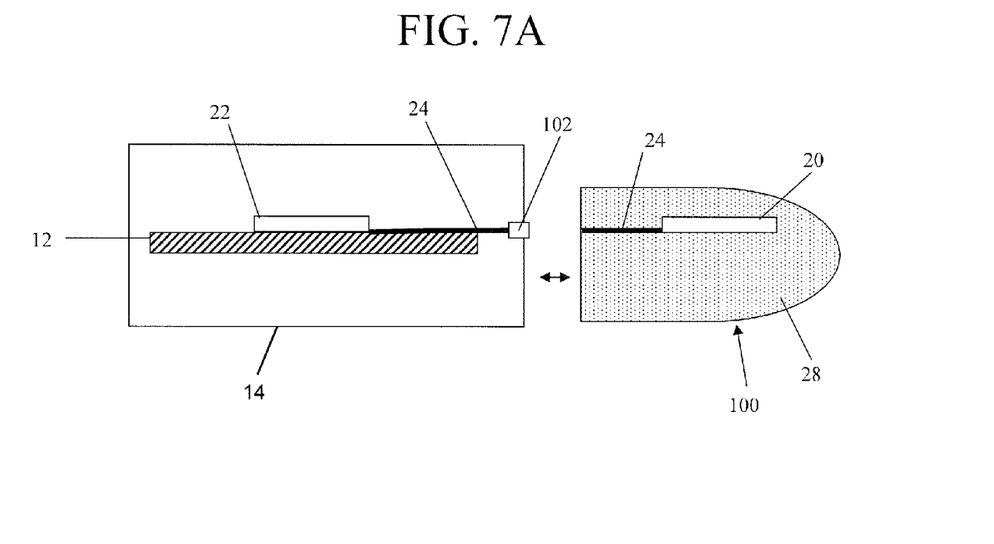
FIGS. 7A and 7B are side, partial cutaway view of respective exemplary implantable medical devices having a cofired, conformally-shaped antenna portion in accordance with one or more embodiments of the present disclosure.
Figure 7B:
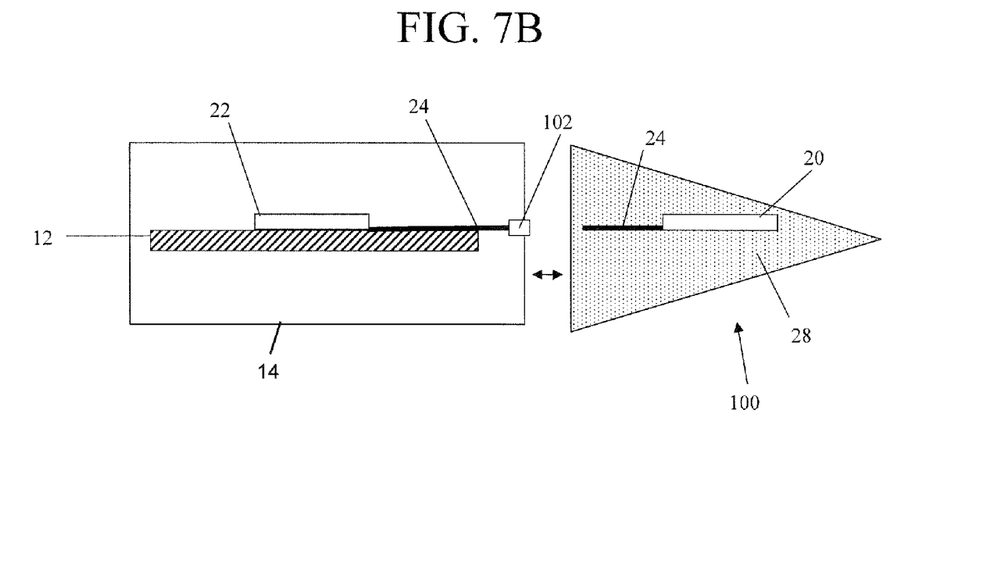
Figure 8A:
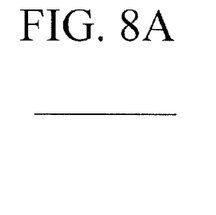
FIGS. 8A-8G are exemplary possible types of antenna arrangements in accordance with one or more embodiments of the present disclosure.
Figure 8B:
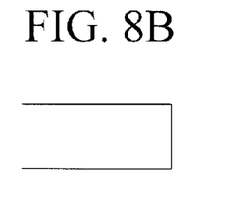
Figure 8C:
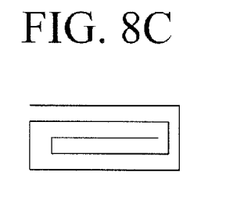
Figure 8D:
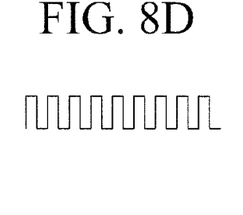
Figure 8E:
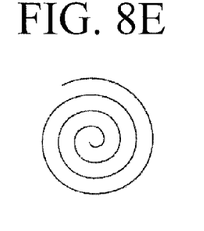
Figure 8F:
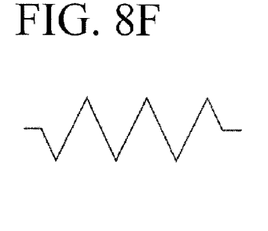
Figure 8G:
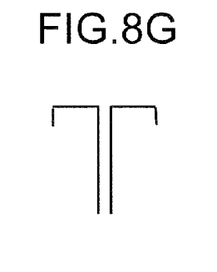

In one or more alternative embodiments, the use of a cofiring technique allows a separate ceramic monolithic structure 100 to be produced, as illustrated in FIGS. 7A and 7B, in which antenna 20 is embedded within a conformally-shaped ceramic hermetic covering 28. In such arrangements, separate ceramic monolithic structure 100 is then joined to housing 14 by sealing monolithic structure 100 to housing 14 at their junction by brazing, glassing, diffusion bonding or other suitable bonding techniques that will provide a hermetic seal, as known to those skilled in the art. In some embodiments, antenna 20 would then be coupled to RF module 22 via an RF feedthrough 102, as known to those skilled in the art. In one or more embodiments, a common housing 14 can be designed for all possible uses of the IMD 10, whereas different shapes for ceramic hermetic covering 28 can be selectively formed (e.g., as illustrated by the different possible shaped ceramic monolithic structures 100 of FIGS. 7A and 7B) based on the desired shape and characteristics of IMD 10. Further, ceramic materials used to form monolithic structure 100 offer the ability to embed passive components to spatially and functionally tailor the dielectric constant or capacitance to optimize packaging efficiency and/or performance.

In one or more embodiments, the ceramic monolithic structure 100 can be formed from one or more layers or sheets of materials (or segments of tape) that comprise the hermetic covering 28, antenna 20 and electrical interconnect 24 may be printed with a metalized paste and other circuit patterns, stacked on each other, laminated together and subjected to a predetermined temperature and pressure regimen, and then fired at an elevated temperature(s) during which the majority of binder material(s) (present in the ceramic) and solvent(s) (present in the metalized paste) vaporizes and/or is incinerated while the remaining material fuses or sinters. In some embodiments, the materials suitable for use as cofireable conductors for forming the antenna 20 are biocompatible metal materials described herein or other materials suitable for the metalized paste. In one or more embodiments, the stacked laminates are then co-fired together at temperatures between about 850° C. and 1150° C. for LTCC materials and between about 1100° C. and 1700° C. for HTCC materials to form the ceramic monolithic structure 100 having the embedded antenna 20. In some embodiments, the materials suitable for use as cofireable ceramics include alumina ($Al_2O_3$), aluminum nitride, beryllium oxide, Silica ($SiO_2$), Zirconia ($ZrO_2$), glass-ceramic materials, glass suspended in an organic (polymer) binder, or mixtures thereof.

Figure 9:
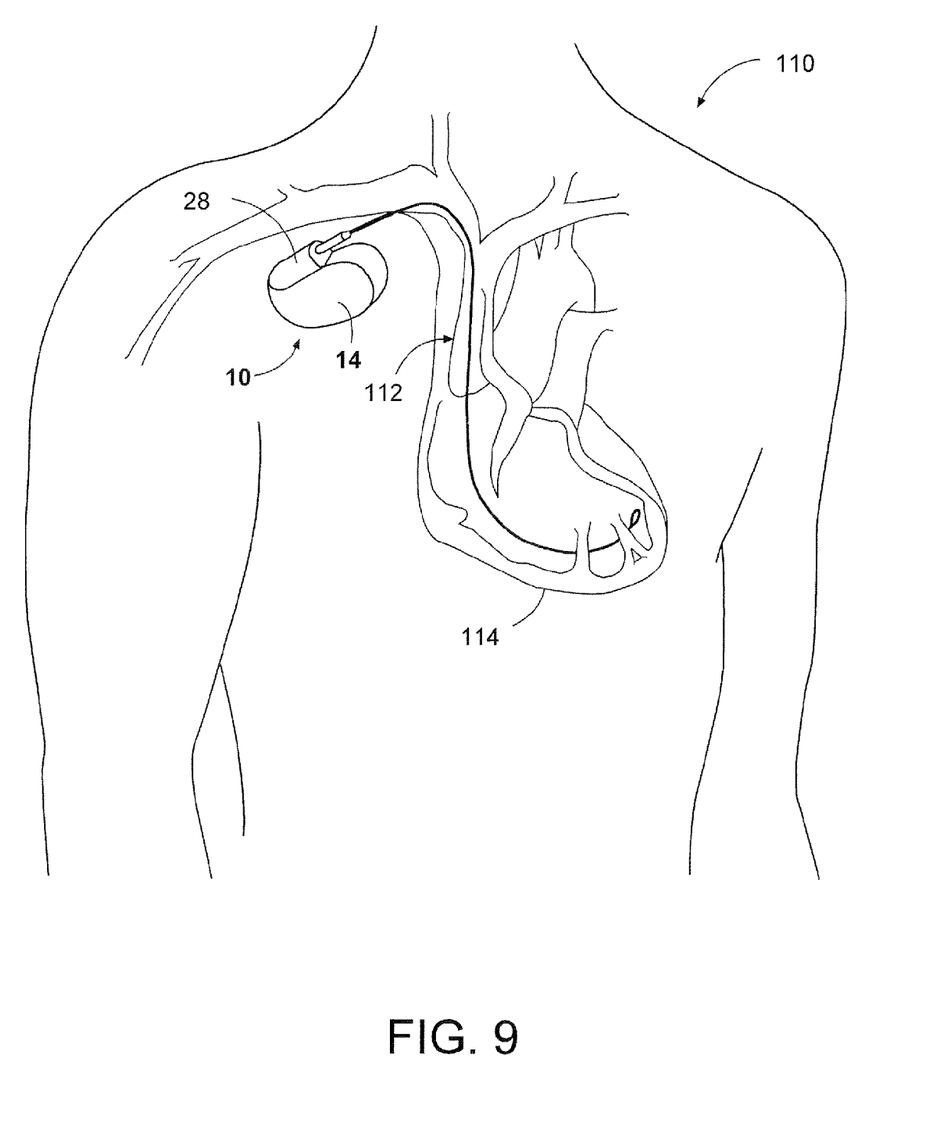
FIG. 9 illustrates an implantable medical device implanted in a human body in accordance with one or more embodiments of the present disclosure.

FIG. 9 is a perspective view of an IMD 10 implanted within a human body 110 in which one or more embodiments of the invention may be implemented. IMD 10 comprises the hermetically sealed housing 14 (or "can") and hermetic cover 28, wherein hermetic cover may further serve as a connector header for coupling IMD 10 to electrical leads and other physiological sensors arranged within body 110, such as pacing and sensing leads 112 connected to portions of a heart 114 for delivery of pacing pulses to a patient's heart 114 and sensing of heart conditions in a manner well known in the art.

For example, such leads may enter at an end of hermetic cover 28 and be physically and electrically connected to conductive receptacles, terminals, or other conductive features located within hermetic cover 28. IMD 10 may be adapted to be implanted subcutaneously in the body of a patient such that it becomes encased within body tissue and fluids, which may include epidermal layers, subcutaneous fat layers, and/or muscle layers. While IMD 10 is depicted in FIG. 9 in a particular configuration, it is understood that this is for purposes of illustration only and IMD 10 may comprise any type of medical device requiring a telemetry antenna.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:

1. An implantable medical device ("IMD"), comprising:
   a housing;
   a monolithic substrate including an interior portion extending within the housing and an exterior portion extending outside of the housing;
   telemetry circuitry connected to the interior portion of the substrate; and
   an antenna formed on the exterior portion of the substrate.

2. The implantable medical device of claim 1, further comprising a hermetic covering positioned around the exterior portion of the substrate covering the antenna.

3. The implantable medical device of claim 2, wherein the hermetic covering comprises a ceramic material.

4. The implantable medical device of claim 3, wherein the hermetic covering comprises a cofired ceramic material conformally shaped based on a desired implantation location for the IMD.

5. The implantable medical device of claim 3, wherein the hermetic covering comprises a cofired ceramic material shaped to provide additional support for the exterior portion of the substrate.

6. The implantable medical device of claim 1, further comprising at least one electrical interconnect formed on the substrate and extending from the exterior portion of the housing to the interior portion for connecting the antenna to the telemetry circuitry.

7. The implantable medical device of claim 6, wherein the at least one electrical interconnect is a controlled impedance line.

8. The implantable medical device of claim 6, wherein the substrate is a circuit board and the electrical interconnect is printed wiring formed on the circuit board.

9. The implantable medical device of claim 1, wherein the exterior portion of the substrate extends outside of the housing a sufficient distance to allow the antenna to be positioned a sufficient distance from the housing to avoid signal interference from the housing.

10. The implantable medical device of claim 1, wherein the antenna is positioned at an end portion of the exterior portion of the substrate so that the antenna can transmit and receive signals in multiple directions from the substrate.

11. The implantable medical device of claim 1, further comprising at least one additional antenna formed on the exterior portion of the substrate.

12. The implantable medical device of claim 11, further comprising a switching device operatively connected to each of the antennas formed on the exterior portion of the substrate for allowing desired ones of the antennas to be selected for use in the antenna.

13. An implantable medical device, comprising:
    a housing;
    a monolithic substrate having an exterior portion and an interior portion, wherein the interior portion is disposed within the housing and the exterior portion is disposed external to the housing;
    an antenna coupled to the exterior portion of the monolithic substrate; and
    telemetry circuitry coupled to the interior portion of the monolithic substrate.

14. The implantable medical device of claim 13, wherein the exterior portion of the monolithic substrate is hermetically coupled at a sidewall of the housing.

15. The implantable medical device of claim 13, wherein an electrical interconnect is embedded within the monolithic substrate to electrically couple the antenna to the telemetry circuitry.

* * * * *